United States Patent
Liu et al.

(10) Patent No.: US 9,188,573 B2
(45) Date of Patent: Nov. 17, 2015

(54) MULTICHANNEL ION CHROMATOGRAPHY SYSTEM AND METHOD

(75) Inventors: Yan Liu, Palo alto, CA (US); Glenn Masami Kuse, Pleasanton, CA (US); Victor Barreto, Campbell, CA (US); Gary L. Gleave, Pleasanton, CA (US); Christopher A. Pohl, Union City, CA (US); William Dale Case, Tracy, CA (US); Khosro Moshfegh, Fremont, CA (US); Michael John McAdams, Los Gatos, CA (US)

(73) Assignee: DIONEX CORPORATION, Sunnyvale, CA (US)

( * ) Notice: Subject to any disclaimer, the term of this patent is extended or adjusted under 35 U.S.C. 154(b) by 813 days.

(21) Appl. No.: 12/690,862

(22) Filed: Jan. 20, 2010

(65) Prior Publication Data
US 2011/0174063 A1 Jul. 21, 2011

(51) Int. Cl.
*G01N 30/02* (2006.01)
*G01N 30/96* (2006.01)
*G01N 30/60* (2006.01)
*G01N 30/88* (2006.01)

(52) U.S. Cl.
CPC ............ *G01N 30/96* (2013.01); *G01N 30/6091* (2013.01); *G01N 2030/8881* (2013.01); *G01N 2030/965* (2013.01)

(58) Field of Classification Search
CPC ............................................. G01N 2030/8881
USPC .................. 422/70; 436/161; 210/198.2, 656; 73/61.52–61.58
See application file for complete search history.

(56) References Cited

U.S. PATENT DOCUMENTS

| | | |
|---|---|---|
| 4,999,098 A | 3/1991 | Pohl et al. |
| 5,248,426 A | 9/1993 | Stillian et al. |
| 5,352,360 A | 10/1994 | Stillian et al. |
| 5,746,976 A | 5/1998 | Yamada et al. |
| 5,766,460 A * | 6/1998 | Bergstrom et al. ........ 210/198.2 |
| 6,036,921 A | 3/2000 | Small et al. |
| 6,068,770 A | 5/2000 | Niermeyer et al. |
| 6,225,129 B1 | 5/2001 | Liu et al. |
| 6,315,954 B1 | 11/2001 | Small et al. |
| 6,316,270 B1 | 11/2001 | Small et al. |
| 6,316,271 B1 | 11/2001 | Small et al. |
| 6,325,976 B1 | 12/2001 | Small et al. |

(Continued)

FOREIGN PATENT DOCUMENTS

| | | |
|---|---|---|
| DE | 19546952 A1 | 6/1996 |
| DE | 19954855 C1 | 4/2001 |
| JP | 03004165 | 1/1991 |

OTHER PUBLICATIONS

ICS-3000 Ion Chromatogrpahy System, Dionex, 2006.*

*Primary Examiner* — Jan Ludlow
(74) *Attorney, Agent, or Firm* — Victor Johnson

(57) ABSTRACT

An ion chromatography housing for easy insertion and removal of a plurality of component cartridges is disclosed. Various components of the IC system are provided in the separate component cartridges. The IC housing includes a capillary separation column and may be connected to conventional-scale components of an IC system. A plurality of IC housings may be provided in a compartment with one or more separation columns. The columns may be capillary columns or conventional-scale columns. A method of using the ion chromatography system is also disclosed. The IC system may be utilized to perform two-dimensional ion chromatographic separation.

20 Claims, 14 Drawing Sheets

(56) References Cited

U.S. PATENT DOCUMENTS

| | | | |
|---|---|---|---|
| 6,613,224 B1 * | 9/2003 | Strand | 210/198.2 |
| 6,682,701 B1 | 1/2004 | Liu et al. | |
| 6,832,622 B2 | 12/2004 | Hassel et al. | |
| 6,942,785 B2 * | 9/2005 | Bayer et al. | 210/91 |
| 2003/0132163 A1 | 7/2003 | Srinivasan et al. | |
| 2005/0252774 A1 | 11/2005 | Anderson, Jr. et al. | |
| 2006/0057733 A1 | 3/2006 | Liu et al. | |
| 2007/0065343 A1 | 3/2007 | Srinivasan et al. | |
| 2008/0173587 A1 | 7/2008 | Srinivasan et al. | |
| 2009/0101582 A1 | 4/2009 | Liu et al. | |
| 2009/0188798 A1 | 7/2009 | Riviello | |

* cited by examiner

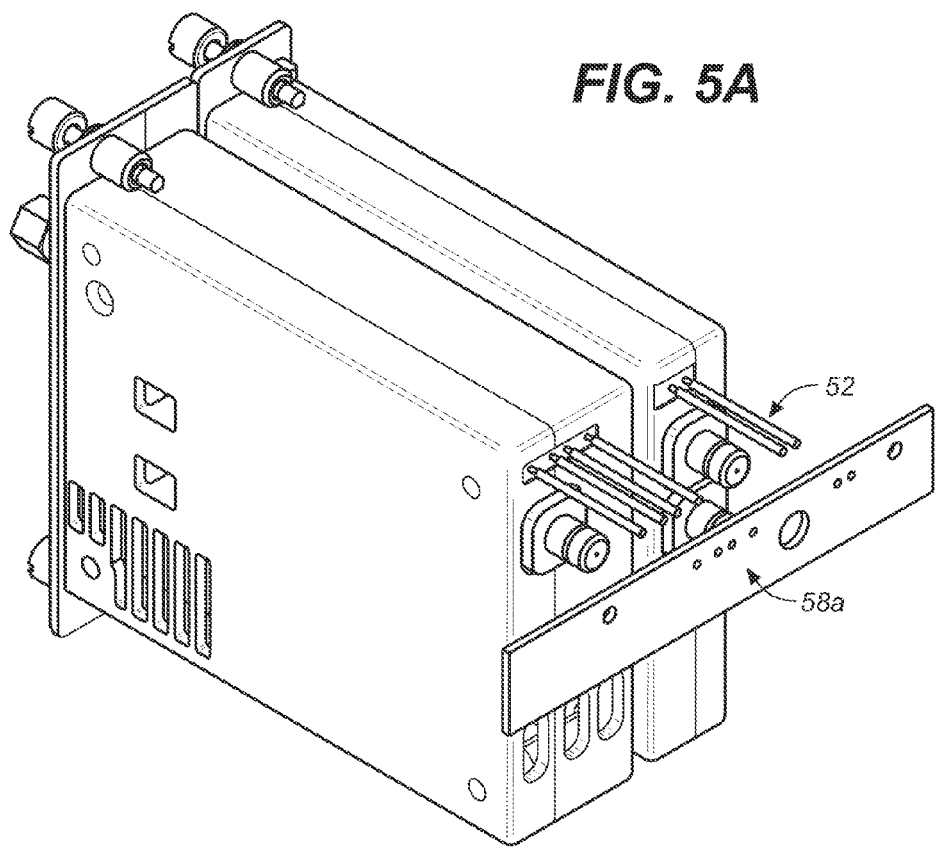

MULTICHANNEL ION CHROMATOGRAPHY SYSTEM AND METHOD

BACKGROUND OF THE INVENTION

1. Field of the Invention

The present invention relates, in general, to ion chromatography systems for determination of both anionic and cationic analytes and methods for their use.

2. Description of Related Art

Ion chromatography (IC) is a widely used analytical technique for the determination of anionic and cationic analytes in various sample matrices. Ion chromatography today is performed in a number of separation and detection modes. Ion chromatography with suppressed conductivity detection is the most widely practiced form of the technique. In suppressed conductivity detection, an eluent suppression device, termed a suppressor, converts the eluent into a weakly conducting form and enhances the conductance of target analytes. The original suppressors were columns packed with ion-exchange resins in appropriate ionic forms. Those packed-bed suppressors had a relatively large dead volume and required off-line chemical regeneration. To overcome this problem, suppressors based on ion-exchange fibers and other membranes were developed. These suppressors can be continuously regenerated using either acid or base regenerant solutions.

One disadvantage associated with the original membrane suppressors was that an external source of either acid or base regenerant solution typically was used to generate the suppressor continuously. Over the years, various designs of electrolytically-regenerated membrane suppressors have been developed to overcome the limitations associated with the chemically-regenerated membrane suppressors. Exemplars of the electrolytically-regenerated membrane suppressors are disclosed by U.S. Pat. Nos. 4,999,098, 5,248,426, 5,352,360, and 6,325,976, the entire contents of which are incorporated herein by reference for all purposes. Electrolytic suppressors offer several advantages in ion chromatography. They provide continuous and simultaneous suppression of eluents, regeneration of the suppression medium, and sufficient suppression capacity for common ion chromatography (IC) applications. They are easy to operate because the suppressed eluent or water can be used to create regenerant ions electrolytically. Thus, there is no need to prepare regenerant solutions off-line. Also, the suppressors are compatible with gradient separations. They also have very low suppression zone volume, which makes it possible to achieve separations with high chromatographic efficiency.

In ion chromatography, dilute solutions of acids, bases, or salts are commonly used as chromatographic eluents. Traditionally, these eluents are prepared off-line by dilution with reagent-grade chemicals. Off-line preparation of chromatographic eluents can be tedious and prone to operator errors, and often introduces contaminants. For example, dilute NaOH solutions, widely used as eluents in the ion chromatographic separation of anions, are easily contaminated by carbonate. The preparation of carbonate-free NaOH eluents is difficult because carbonate can be introduced as an impurity from the reagents or by adsorption of carbon dioxide from air. The presence of carbonate in NaOH eluents can compromise the performance of an ion chromatographic method, and can cause an undesirable chromatographic baseline drift during the hydroxide gradient and even irreproducible retention times of target analytes. In recent years, several approaches that utilize the electrolysis of water and charge-selective electromigration of ions through ion-exchange media have been investigated by researchers to generate high-purity ion chromatographic eluents. U.S. Pat. Nos. 6,036,921, 6,225,129, 6,316,271, 6,316,270, 6,315,954, and 6,682,701, the entire contents of which are incorporated herein by reference for all purposes, describe electrolytic devices that can be used to generate high purity acid and base solutions by using water as the carrier. Additionally, U.S. Patent Publication Nos. 2003/0132163 and 2008/0173587, incorporated herein by reference for all purposes, describe trap columns that are regenerated electrolytically for removing contaminant ions from eluents and purifying the eluent stream. In one embodiment, the eluent stream flows through a purifying flow channel, including an ion exchange bed. An electric field is applied through the flowing eluent stream in the purifying flow channel, and the contaminant is removed from the eluent stream. Using these devices, high purity, contaminant-free acid or base solutions are automatically generated on-line for use as eluents in chromatographic separations. These devices simplify gradient separations that can now be performed using electrical current gradients with minimal delay instead of using a conventional mechanical gradient pump.

The combined use of the electrolytic eluent generator and suppressor has significantly changed the routine operation of ion chromatographic methods and permits the performance of various ion chromatographic separations using only deionized water as the mobile phase. The use of these electrolytic devices results in significant improvements in the performance of ion chromatography methods by allowing minimal baseline shifts during the gradients, greater retention time reproducibility, lower detection backgrounds, and lower detection limits for target analytes.

There has been a continuing interest in using capillary ion chromatography using separation columns with internal diameters of 1 mm or smaller as an analytical separation tool because of the perceived advantages associated with the miniaturization of separation processes. To date, such systems have not been employed because of the lack of suitable instrumentation and consumables. Typical separation columns in conventional-scale ion chromatography have column internal diameters ranging 2 mm to 9 mm and are operated in flow rate ranging from 0.2 to 5 mL/min.

U.S. Patent Application Publication No. 2006/0057733, the entire content of which is incorporated herein by reference for all purposes, discloses a capillary ion chromatography system using electrolytic generation of potassium hydroxide eluents and suppressed conductivity detection for determination of anions. In this system, the capillary pumping system is used to deliver a stream of deionized water into the capillary KOH eluent generator which consists of a high pressure generation chamber containing a Pt cathode and a low pressure electrolyte reservoir containing a Pt anode. Under the applied electrical field, the potassium ions migrate across the ion exchange connector to combine with hydroxide ions to form a KOH eluent. The concentration of KOH solution formed is proportional to the applied current and inversely proportional to the flow rate of the deionized water carrier stream. Other downstream system components include a degasser unit, an injector, a separation column, a suppressor and a detector.

U.S. Patent Application Publication No. 2006/0057733 further discloses several embodiments of capillary ion chromatography suppressors. In one embodiment, the capillary anion suppressor consists of three chambers. The eluent chamber contains a cation exchange capillary tubing embedded tightly inside a bed of cation exchange resin. Provisions are made so that there are separate fluid connections to the cation exchange capillary tubing in the resin bed. The eluent chamber is physically separated from the cathodic regenerant chamber and anodic regenerant chamber through cation exchange ion exchange membranes. The cathode chamber contains a perforated Pt cathode and the anode chamber contains a perforated Pt anode. Both electrode chambers have two liquid connecting ports (inlet and outlet). In the operation of this type of electrolytic capillary suppressor, the resin bed is continuously regenerated by hydronium ions generated through the electrolysis of water at the device anode. Under the applied electrical field, the hydronium ions generated at the anode of the device migrate across the cation exchange membrane into the cation exchange resin bed. In the meantime, potassium ions exchanged onto the resin bed also migrate across the other cation exchange membrane into the device cathode chamber before going to waste. Water used in electrolysis can be derived from the aqueous effluent from the conductivity detector.

In ion chromatography systems, users need to make a large number of fluid or liquid connections among various system components. To ensure the optimal chromatographic performance, it is critical to ensure that fluid connections are made properly and free of dead volume. For capillary ion chromatography, making proper fluid connections can be very difficult to accomplish because dead volumes as small as several nanoliters can have a dramatically adverse impact on the system performance when the separation flow rates are on the order of several microliters per minute.

In recent years, the use of automated two-dimensional IC methods has gained increasing interest in the determination of analyte ions in environmental samples because those methods provide convenient on-line matrix elimination or diversion and eliminate the needs for cumbersome off-line sample pretreatment steps. In one exemplary two-dimensional IC method, analyte ions are partially resolved from matrix ions on a conventional IC column (e.g., 4-mm ID) in the first dimension, collected onto a capillary concentrator column, then resolved from residual matrix ions on another IC column in the second dimension. The suppressed effluent from the hydroxide eluent in the first dimension is water, which provides the ideal environment for ion-exchange retention and concentration before the transfer to the second dimension. If a 0.4-mm ID (Inner Diameter) capillary IC column is used in the second separation dimension, the column has a one-hundredth cross-sectional area relative to the first dimension column, detection sensitivity is enhanced by a factor of 100. In addition, the two-dimensional IC method makes it possible to combine two different column chemistries. Two-dimensional IC methods with both suppressed conductivity and mass spectrometry detection would provide the advantages of using these methods for determination of parts-per-trillion levels of analyte of interests such as perchlorate and bromate in environmental samples.

Therefore, there are needs to develop capillary ion chromatographs that provide improved means for fluid connections to make capillary ion chromatography a more ease-to-use and reliable analytical technique. In additions, there is also the need to develop multichannel ion chromatographs that offer improved and ease-to-use integration of ion chromatographic separation processes at conventional flow rates and capillary flow rates.

In light of the foregoing, it would be beneficial to have methods and apparatuses which overcome the above and other disadvantages of known ion chromatography systems.

BRIEF SUMMARY OF THE INVENTION

Various aspects of the present invention relate to multichannel ion chromatography systems using electrolytic eluent generation and suppressed conductivity detection. In summary, various aspects of the present invention are directed to an apparatus for ion chromatography (IC) comprising a sample injector for providing a sample having a target analyte or target analytes, an IC separation column for separating ionic species in the sample, the separation column housed within a separation column cartridge, an suppressor for reducing the conductance of the eluent and enhancing the conductance of the target analyte, the suppressor housed within a suppressor cartridge, and a miniaturized IC housing removably receiving the separation column cartridge and suppressor cartridge within respective predefined separation column and suppressor spaces.

In various embodiments, the apparatus includes a high-pressure degasser assembly cartridge for removing gas from the eluent. In various embodiments, the apparatus includes a carbonate removal device cartridge fluidly connected to the suppressor. The degasser assembly cartridge and carbonate removal device cartridge are received in carbonate removal device and degasser assembly spaces in the housing. Each of the cartridges may include quick fluid connectors. In various embodiments, the apparatus includes a regenerant manifold plate attached to the quick fluid connectors of at least two of the cartridges and configured to direct a regenerant flow among the respective cartridges.

The apparatus may include a temperature-controlled zone in the housing for maintaining a temperature of the separation column cartridge. The temperature-controlled zone may include a heating element.

Various aspects of the present invention are directed to a modular system employing modular component cartridges. In various embodiments, each of the respective cartridges comprises a circuit board for controlling respective internal components. Each of the respective cartridges optionally includes at least one electrical pin connector connected at one end to the circuit board and an opposite end to establish an electrical connection with a main circuit board provided in the housing when the respective cartridge is engaged within the housing. In various embodiments, one or more of the cartridges is replaced by a bypass cartridge that includes fluid connection lines instead of actual system components.

In various embodiments, the housing is block-shaped and the predefined spaces are slots for receiving the cartridges. The exemplary housing has a volume in the range of about 1 cubic inch to about 1000 cubic inches. In various embodiments, the miniaturized IC housing is configured for insertion into a larger compartment of an ion chromatography system for connecting with other system components.

In various embodiments, a second IC apparatus is housed within a second housing. The second IC housing may be a miniaturized IC housing. The second IC housing may be positioned side-by-side in the system compartment with the first IC housing. In various embodiments, the second IC apparatus is configured for finer resolution than the first IC apparatus. In various embodiments, the compartment includes one or more conventional-scale separation columns. In various embodiments, the first and/or second IC housing includes a capillary-scale separation column.

Various aspects of the present invention are directed to a system for ion chromatography comprising the above apparatus for ion chromatography in combination with an eluent generator driven by a pump for delivering eluent to the sample injector, and a detector fluidly connected to the suppressor directly or via the carbonate removal device for detecting an resolved ionic species. The system may include a pump. In various embodiments, the apparatus for ion chromatography, eluent generator, and detector are capillary-scale components and the pump is conventional-scale.

In various embodiments, the system includes a concentrator column for receiving and concentrating treated effluent from the IC separation column, a second IC separation column in fluid communication with the concentrator column, a second suppressor in fluid communication with the second separation column, and a second detector for detecting a resolved ionic species from the second suppressor. In various embodiments, the concentrator column, second IC separation column, and second suppressor are housed in the miniaturized IC housing.

In various embodiments, the eluent generator is an electrolytic eluent generator. In various embodiments, the detector is a conductivity detector. In various embodiments, the suppressor is an electrolytic suppressor.

Various aspects of the present invention are directed to a method of performing ion chromatography comprising loading the system with a sample, flowing the sample in the system, and detecting resolved species in the detector.

Various aspects of the present invention are directed to a system for ion chromatography comprising a sample injector for delivering a sample including a target analyte or target analytes, an eluent generator for delivering eluent to the sample injector, an IC housing assembly, and a detector fluidly connected to the carbonate removal device for detecting a resolved ionic species. In various embodiments, the IC housing assembly includes a degasser assembly cartridge including a high-pressure degasser assembly for removing gas from the eluent, a separation column cartridge including an IC separation column for separating ionic species from the target analyte, a suppressor cartridge including an suppressor for enhancing the conductance of the target analyte, a carbonate removal device cartridge fluidly connected to the suppressor, and a miniaturized housing for removably receiving each of the cartridges in predefined slots.

In various embodiments, the system includes a second IC housing assembly connected to a second injector and second eluent generator, the second IC housing assembly comprising a second degas assembly, a second IC separation column, a second suppressor, and a second carbonate removal device; and a second detector fluidly connected to the carbonate removal device for detecting a resolved ionic species. The first separation column may be a capillary-scale separation column and the second separation column may be a conventional-scale separation column. The first separation column may be a conventional-scale separation column and the second separation column may be a capillary-scale separation column.

Various aspects of the present invention are directed to an ion chromatography system comprising a regenerant manifold plate. In various embodiments, the manifold plate includes a plurality of fluid connectors for establishing quick fluid connections, the manifold plate including a number of fluid connectors based on a number of regenerant chambers. The manifold plate may be configured to direct a regenerant flow among the respective regenerant chambers. The system may be used in combination with a degasser assembly cartridge, a separation column cartridge, and a suppressor cartridge. The system may be used with a carbonate removal device cartridge. The cartridges may each include connectors for establishing a fluid connection with respective connectors on the manifold plate. Each of the connectors may include a sealing member for ensuring a fluid-tight seal with the corresponding connector of the respective cartridge.

Various aspects of the present invention are directed to an apparatus for ion chromatography (IC) comprising a sample injector for providing a sample having a target analyte or target analytes; an IC separation column for separating ionic species in the sample; a suppressor for reducing the conductance of the eluent and enhancing the conductance of the target analyte; a bypass cartridge including fluid connections defining a flow channel; and a miniaturized IC housing configured to house the sample injector, IC separation column, and suppressor. The IC housing removably receives the bypass cartridge within a respective predefined bypass cartridge space to fluidly connect one of the sample injector and the separation column, the separation column and the suppressor, and a combination of the same.

The ion chromatography apparatus and method of the present invention(s) have other features and advantages which will be apparent from or are set forth in more detail in the accompanying drawings, which are incorporated in and form a part of this specification, and the following Detailed Description of the Invention, which together serve to explain the principles of the present invention(s).

BRIEF DESCRIPTION OF THE DRAWINGS

FIG. 5A is a perspective view of the back end of the IC cube of FIG. 2, illustrating an array of pin connectors on the back of each cartridge connected to a respective circuit board so each cartridge can easily establish an electrical connection with the IC cube back panel when the cartridge is installed or inserted.

DETAILED DESCRIPTION OF THE INVENTION

Reference will now be made in detail to the various embodiments of the invention, examples of which are illustrated in the accompanying drawings. While the invention will be described in conjunction with the various embodiments, it will be understood that they are not intended to limit the invention to those embodiments. On the contrary, the invention is intended to cover alternatives, modifications and equivalents, which may be included within the spirit and scope of the invention as defined by the appended claims.

Figure 1:
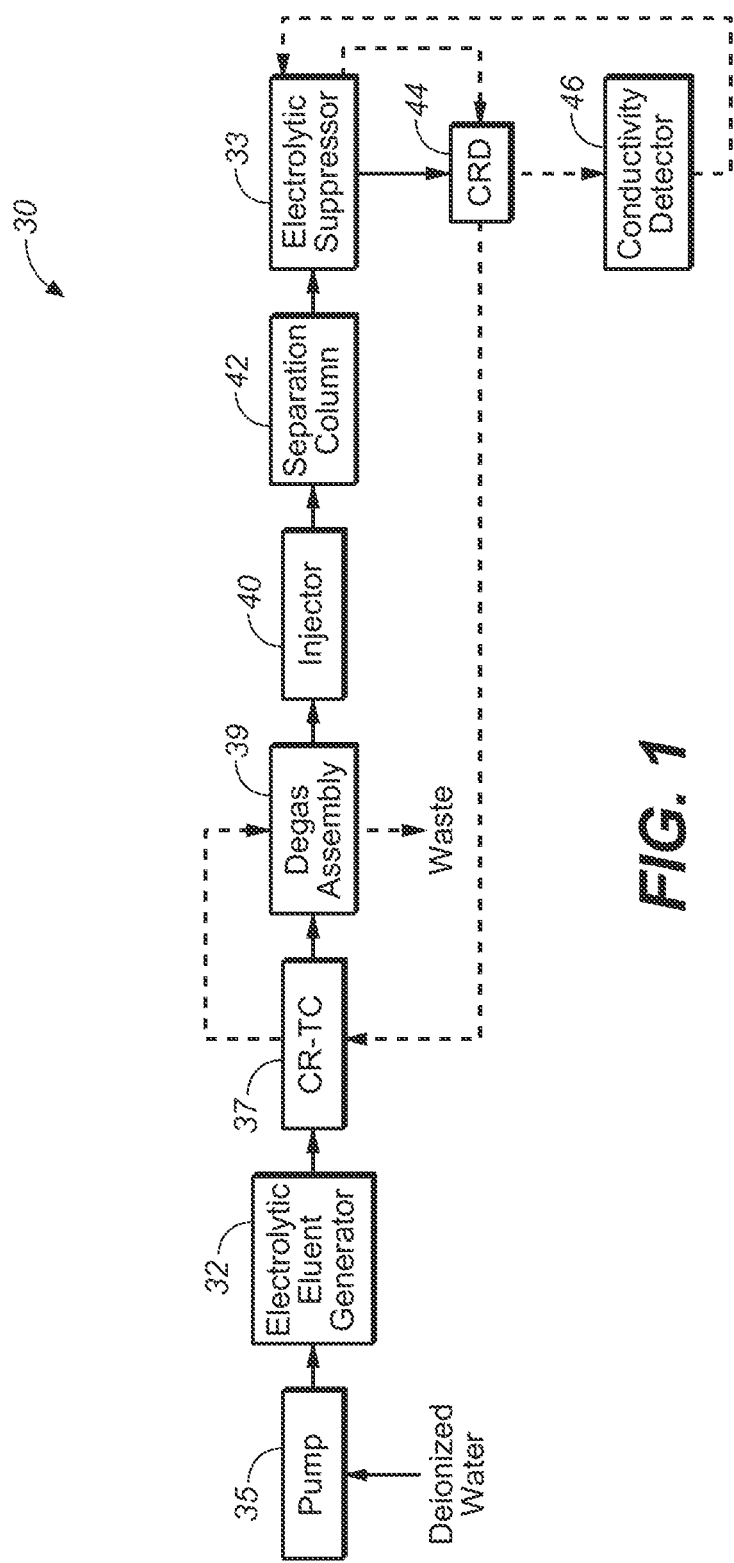
FIG. 1 is a block diagram of an exemplary ion chromatography system using electrolytic generation of eluents and suppressed conductivity detection for determination of anions or cations in accordance with the present invention.

Turning now to the drawings, wherein like components are designated by like reference numerals throughout the various figures, attention is directed to FIG. 1.

FIG. 1 is a block diagram representing an exemplary ion chromatography (IC) system, generally designated 30, using electrolytic generation and suppressed conductivity detection. The exemplary system includes an electrolytic eluent generator (EG) 32 and electrolytic suppressor 33, but one will appreciate from the following description that other generators, suppressors, and configurations may be used in accordance with the present invention, for example non-electrolytic generators and suppressors. Exemplary system 30 makes use of conventional IC components using electrolytic generation of potassium hydroxide eluents and suppressed conductivity detection for determination of anions. One will appreciate that the exemplary system may also use MSA eluents and suppressed conductivity detection for determination of cations. In many aspects, eluent generator 32 is similar to those described in U.S. Pat. Nos. 6,036,921, 6,225,129, 6,316,271, 6,316,270, 6,315,954, and 6,682,701 and U.S. Patent Publication Nos. 2003/0132163, 2006/0057733, and 2008/0173587, the entire contents of which are incorporated herein by reference for all purposes. In many aspects, suppressor 33 is similar to those described in U.S. Pat. Nos. 4,999,098, 5,248,426, 5,352,360, and 6,325,976, the entire contents of which patents are incorporated herein by reference for all purposes.

In the exemplary system, a pump 35 is used to deliver a stream of deionized water into eluent generator cartridge 32, which includes a KOH eluent generator and a high pressure generation chamber containing a Pt cathode and a low pressure electrolyte reservoir containing a Pt anode. Under the applied electrical field, the potassium ions migrate across the ion exchange connector to combine with hydroxide ions to form a KOH eluent. The concentration of KOH solution formed is proportional to the applied current and inversely proportional to the flow rate of the deionized water carrier stream.

Exemplary system 30 optionally includes a continuously regenerated anion trap column (CR-ATC) 37 downstream from the electrolytic eluent generator for removing trace contaminants in the eluent. One will appreciate that the CR-ATC may be substituted with other traps depending on the application. The other downstream system components include a high-pressure degasser assembly 39 used to remove hydrogen gas formed by the electrolytic operation of the KOH eluent generator and CR-ATC, a sample injector 40, a separation column 42, electrolytic suppressor 33, a carbonate removal device (CRD) 44, and a conductivity detector 46. Effluent exiting the conductivity detector is routed through the regenerant chambers of the electrolytic suppressor, the CRD, the CR-ATC, and the high-pressure degasser assembly before going to waste 47.

As will be described in greater detail below, any number of the illustrated components may be housed within modular cartridges configured to be removably inserted into a larger structure or compartment. In various embodiments, the eluent generator, suppressor, and degasser assembly are provided in separate, removable cartridges. Throughout the description herein, reference may be made to the system components and respective cartridges interchangeably.

Some of the system components may include manual fluid connectors for forming a fluid channel. In various embodiments, the fluid connectors are 10-32 thread female inlet and outlet fluid connection ports. Several components including the CR-ATC, the high-pressure degasser assembly, and the electrolytic suppressor, and the carbonate removal device also have an additional set of 10-32 or ¼-28 thread female inlet and outlet fluid connection ports for their regenerant chambers. Small-bore polyetheretherketone (PEEK) tubing (e.g., ¹⁄₁₆-inch OD×0.0010-inch to 0.030-inch ID) with nuts and ferrule at each end is optionally used to connect the various components together. To plumb together the various components illustrated in FIG. 1, the operator of the system needs to make at least 16 fluid connections manually to direct the eluent flow from the pump outlet to the conductivity detector inlet. Additionally, the system operator needs to make at least 9 fluid connections manually to direct the regenerant flow through the outlet of conductivity detector to waste.

In various embodiments, the inlet and outlet ports of the various system components are prepared in a manner that the inlet port is a 10-32 or ¼-28 thread male connector and the outlet port is a 10-32 or ¼-28 thread female connector. The system components are connected to each other directly without the need to use a piece of coupling tubing fitted with nuts and ferrules. In the system illustrated in FIG. 1, the number of fluid connections that the system operator needs to make to plumb the various components together is reduced by about half from the system described above. For example, the operator would need to make 8 fluid connections (instead of 16 connections) manually to direct the eluent flow from the pump outlet to the conductivity detector inlet and 5 fluid connections manually (instead of 9 connections) to direct the regenerant flow through the outlet of the conductivity detector to waste. Thus, the described connections simplify and reduce the number of manually-made fluid connections in the ion chromatography system. In the case of a capillary ion chromatography system, improvements in the ease-of-use and reliability of the system provide additional benefits since making proper fluid connections can be particularly difficult to accomplish.

In various embodiments, the system is a capillary ion chromatography system with the separation columns having internal diameters of 1 mm or smaller. A capillary ion chromatography system typically operates at about 1 µL/min to about 20 µL/min. Chromatographic performance can be improved by minimizing the delay volumes or dead volumes of the system components and connections. It is advantageous to minimize the dimension of all system chromatography components and the compartment that houses those components.

Figure 2:
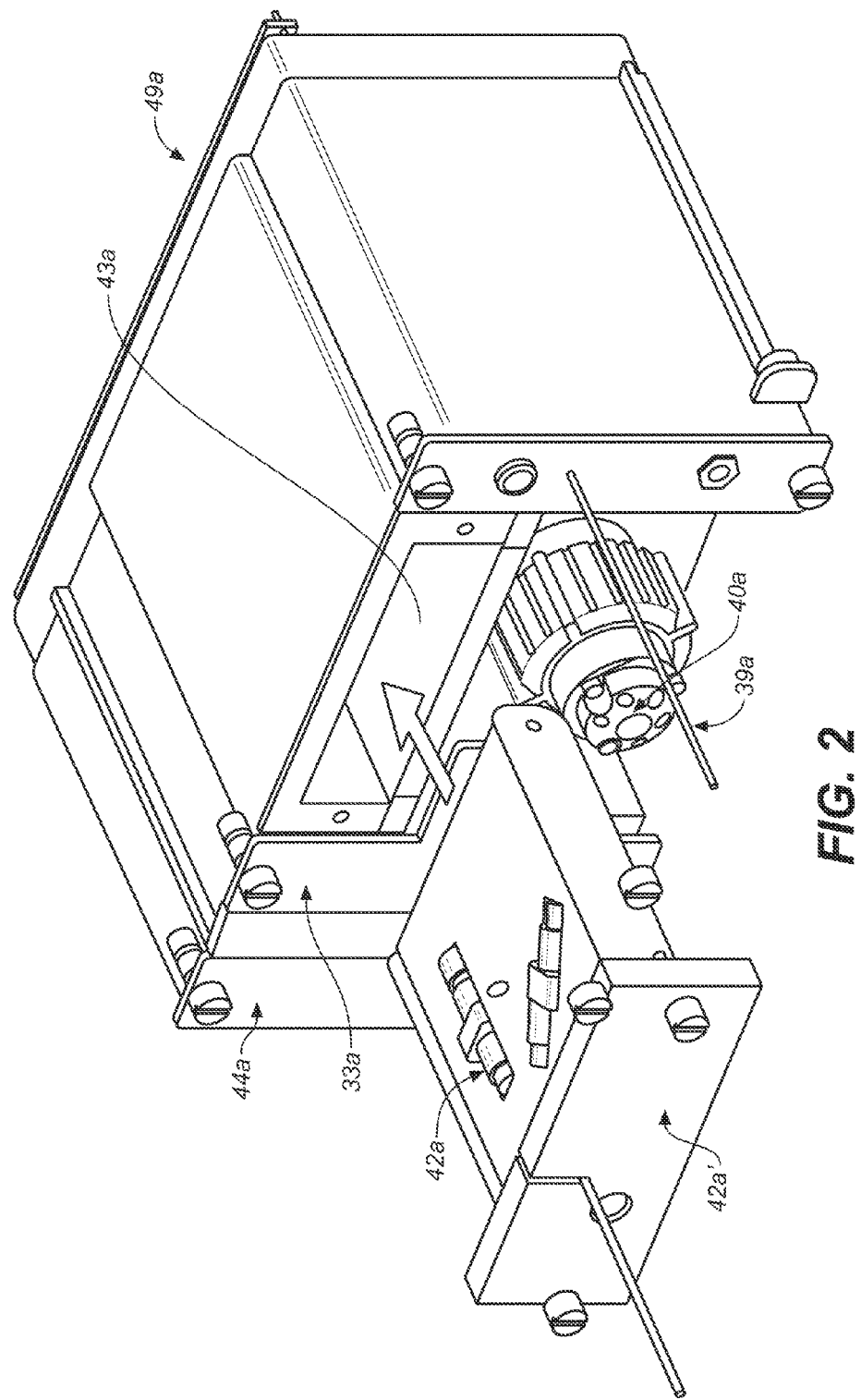
FIG. 2 is a perspective rear view of a miniaturized ion chromatography housing in accordance with the present invention, illustrating housing of several components of the IC system including a capillary column cassette into predefined spaces of a housing fashioned as a cube in accordance with the present invention.

FIG. 2 illustrates a system 30a that minimizes the dimension of most or all of the system chromatography components and the compartment that houses the components. In some respects, system 30a is configured and operates similar to system 30 described above. In various embodiments, the chromatography compartment adopts a form of small cube or housing 49a. Housing and cube will be used interchangeably hereafter to refer to element 49a. One will appreciate from the description herein that housing 49a may have various shapes, configurations, and structures including, but not limited to, a rectangular prism and curved shapes.

IC housing 49a is designed to house several key chromatography components such as a high-pressure degasser assembly 39a, a sample injector 40a, a separation column 42a, an electrolytic suppressor 33a, and a carbonate removal device (CRD) 44a.

In various embodiments, the functional components of each of the high-pressure degasser assembly, the separation column, the electrolytic suppressor, and the carbonate removal device (CRD) are packaged separately into small rectangular cartridges, generally designated 51, configured to be received in the housing. The corresponding cartridges are designated 39a', 40a', 42a', 33a', and 44a', respectively. The cartridges and housing 49a are configured to allow removable insertion of the cartridges into predefined spaces in the housing. The housing and the system component cartridges are designed to provide appropriate mechanical features to allow easy installation and removal of the cartridges into the housing. In various embodiments, the housing includes slots with mechanical fasteners such as clips or latches for easily inserting and retaining the cartridge in the housing and releasing of the cartridge when it needs to be replaced or exchanged. The housing may include guide tracks or other features to ease insertion of the cartridges. The housing may also include slots with predefined shapes or other features to key the slots to a particular cartridge and prevent insertion of a cartridge into the wrong area of the housing.

In various embodiments, one or more of the described above are configured as bypass cartridges. In contrast to cartridges 51, the bypass cartridges contain fluid connection lines instead of actual system components. The fluid lines define a flow channel through the cartridge. The bypass cartridges may be used in the system configurations where component cartridges are not needed such that various functional components of the system may be bypassed. The bypass cartridges may also enable use of IC housing 49a with other instrument configurations. In various embodiments, the bypass cartridge or cassette includes one or more regenerative ports and internal loops or tubing extensions that connect to the front of the cassette for interfacing with other components. In various embodiments, one, two or more functional components of the IC system is housed in the IC housing and the bypass cartridge provides a fluid connection between the one, two, or more components and/or other components of the system.

In various embodiments, separation column 42a is configured as an integrated module and the separation column cartridge 42a' is formed as a cassette for receiving one or more separation column modules. Referring to FIG. 2, the cassette allows for easy removal and substitution of various columns by minimizing the need to change many of the fittings and fluid connections of the system. Instead of disassembling the whole column, a user removes the separation column cassette from a receiving slot 43a and inserts a new cassette or changes one or more of the separation columns in the cassette.

The exemplary sample injector 40a is positioned adjacent to and in fluid communication with the separation column cartridge. In various embodiments, the injector is an injector assembly fixed in the housing. "Fixed" is to be understood as used in the mechanical arts and means that removal of the injector requires removal of permanent fasteners such as screws and the like.

One will appreciate that housing 49a may also be designed to accommodate additional system components such as the electrolytic eluent generator, continuously regenerated trap column (CR-TC), and/or a detector. The detector may be a conductivity detector, an electrochemical detector, or other detector compatible with an ion chromatography system.

Figure 3A:
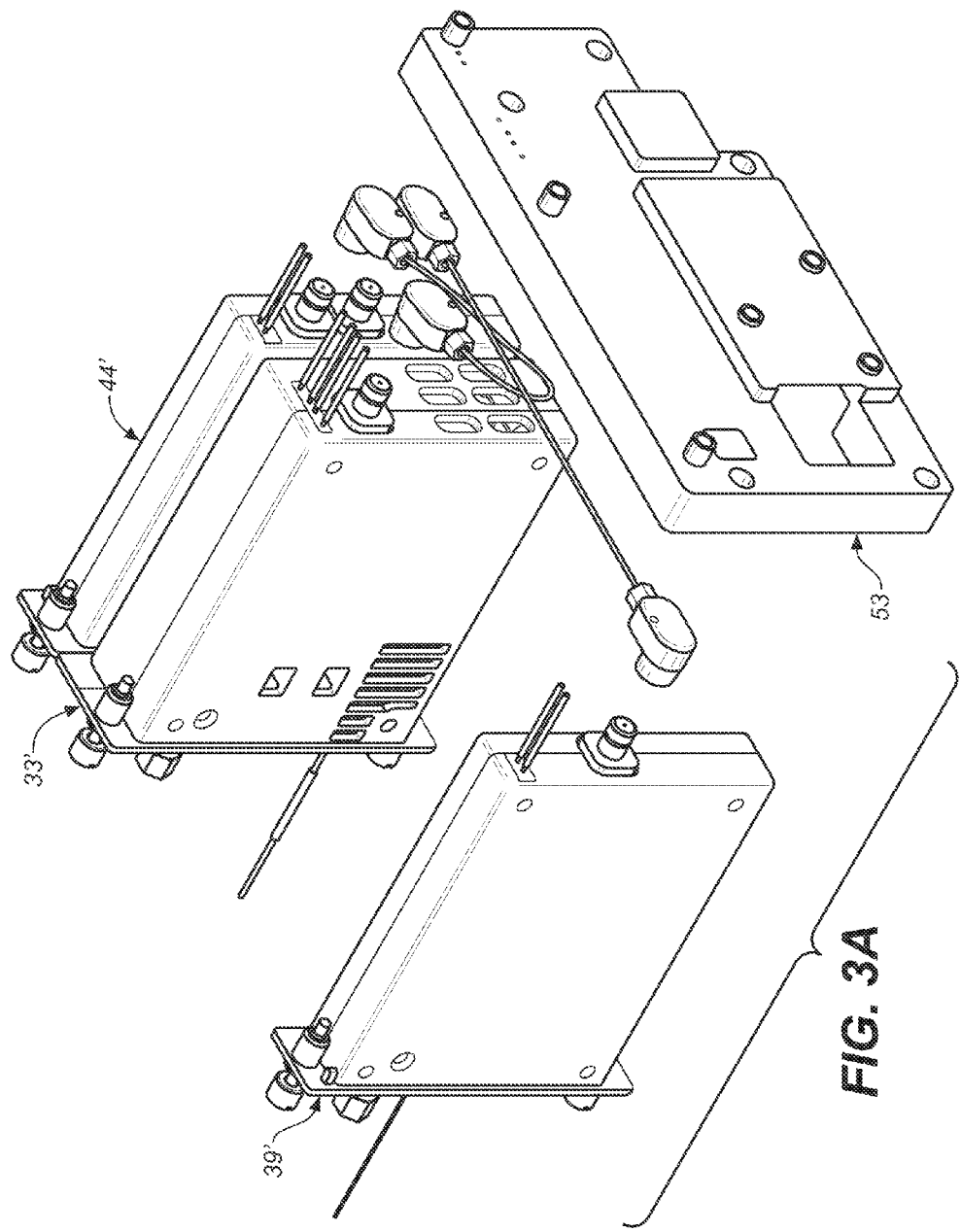
FIG. 3A is a partially exploded view of the cube of FIG. 2 and a regenerant flow manifold plate, illustrating the back panel of various cartridges housed in the IC cube configured with fluid connectors to connect to the manifold plate in accordance with the present invention.
Figure 3B:
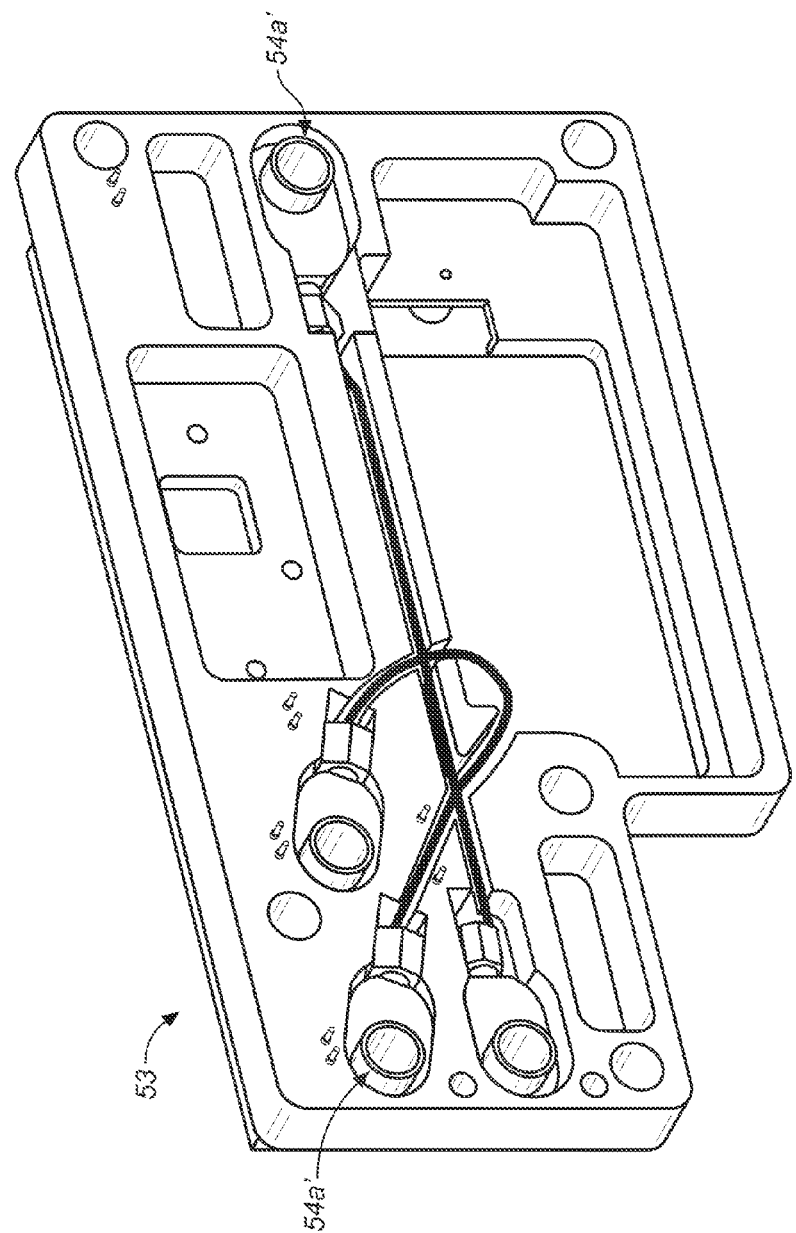
FIG. 3B is an interior perspective view of the regenerant flow manifold plate.
Figure 4:
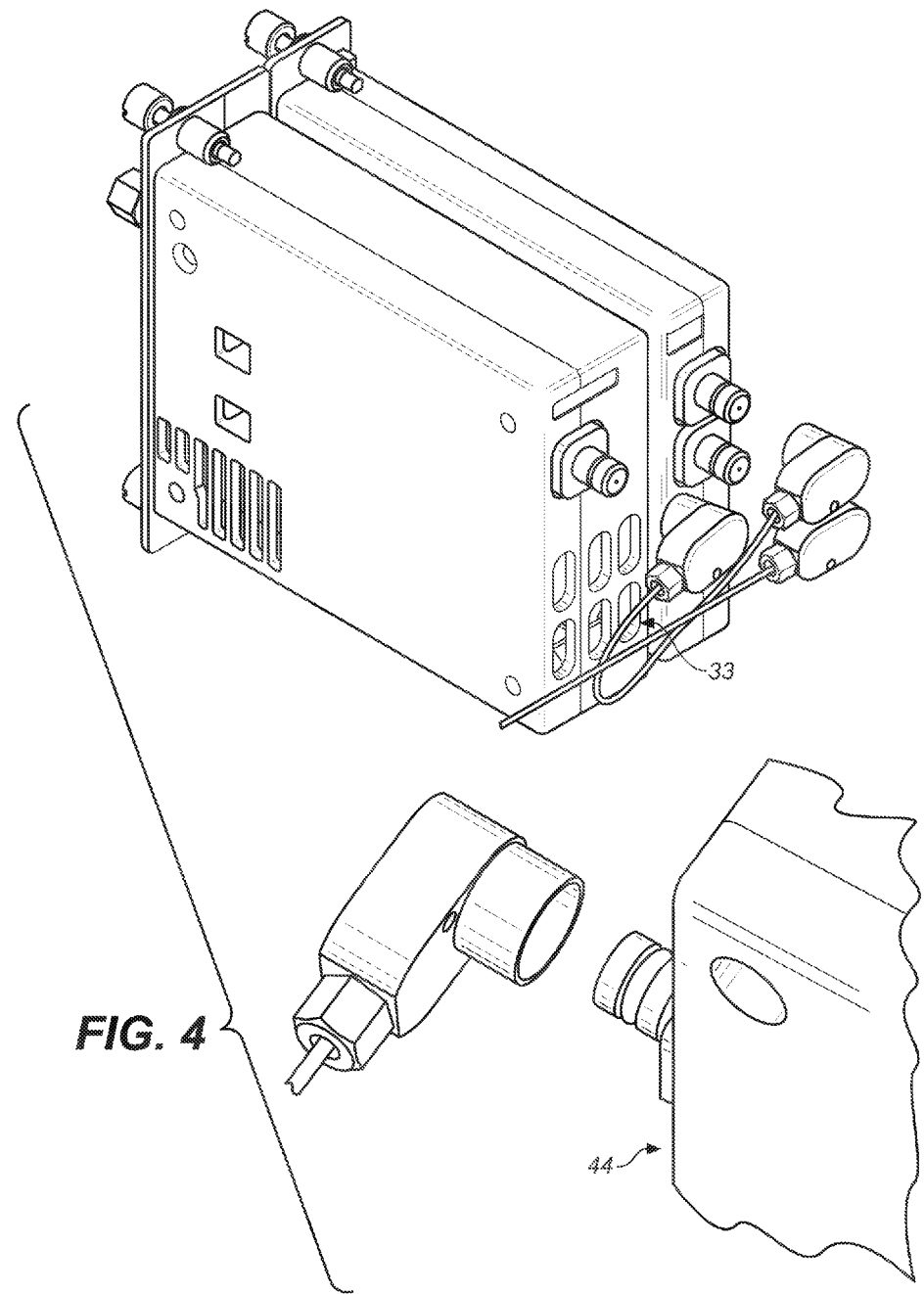
FIG. 4 is an enlarged, rear perspective view of the back of the IC cube and manifold plate of FIG. 3, illustrating connection of the female quick connect/disconnect fluid connectors of the regenerant flow manifold plate with respective male connectors on the regenerant chambers of the IC cartridges in accordance with the present invention.

In various embodiments, the back panel of IC housing 49a is fitted with a regenerant flow manifold plate 53 as shown in FIGS. 3-4. Although the regenerant manifold plate is shown as a plate structure, one will appreciate that any suitable structure or configuration may be used. The exemplary manifold plate attaches to the housing in a conventional manner and includes fluid fittings or connectors 54a for fluidly connecting to the various housing components. The exemplary manifold plate includes an appropriate number of female quick connect/disconnect fluid connectors to direct the regenerant flow among the regenerant chambers of the various components in the system. The cartridges with regenerant chambers (e.g., the high pressure degas assembly, the electrolytic suppressor, and the CRD) are fitted with male quick connect/disconnect fluid connectors corresponding to female fluid connectors on the manifold plate.

In various embodiments, each of fluid connectors 54a includes a sealing member 56a to ensure a fluid-tight seal between the connector on the manifold plate and respective chamber. The fluid sealing of the exemplary quick connect/disconnect connectors is accomplished through the use of o-rings formed of a material that is chemically compatible with the eluents used in ion chromatography. Each female quick connect/disconnect fluid connector includes another female fluid outlet port with 10-32 or ¼-28 threads. The exemplary fluid connectors are connected together using small-bore PEEK tubing (e.g., ¹⁄₁₆-inch OD×0.001-inch to 0.040-inch ID) with appropriate nuts and ferrules at each end.

The regenerant flow enters manifold plate 53 through a first fluid connector and is directed in the manifold plate via fluidic components or integral fluid channels to a second fluid connector thereby facilitating flow from one chamber to another. In this manner, the regenerant manifold plate of the IC cube serves to direct the regenerant flow among the regenerant chambers of the various components in the system.

Exemplary IC housing 49a includes five fluid connections to internal cartridges 51 and up to four regenerative fluid connectors. These five connections may be pre-made during the manufacture of the components to allow easy set-up by the user. Tubing thus exits the front of each cartridge, which is already internally connected, so a user only needs to connect the one loose end of the tube to the system. This allows for about nine few connections than a user typically makes in a conventional system, which provides greater ease-of-use and reduces the chance of errors.

The design of IC housing 49a with regenerant manifold plate 53 and the related component cartridges allows fast, simple insertion of key IC system components into IC housing 49a, and consequently IC system 30, and provides automatic fluidic connections for regenerant flows. This significantly simplifies and reduces the number of manually-made fluid connections in the ion chromatography system. In the case of a capillary ion chromatography system, this can be especially beneficial and improve the system's ease-of-use and reliability since making proper fluid connections can be particularly difficult to accomplish in capillary ion chromatography systems. The design also significantly reduces the scale and dimensions of the components of the system.

In various embodiments, IC housing 49a includes appropriate electronics circuit boards 58a that can be used to provide current and/or voltage power sources required for operation of various in the cartridge. For example, electrolytic eluent generator 32a, electrolytic suppressor 33a, and CR-ATC 37a may have circuit boards for providing power and control to the respective internal cartridge components.

In various embodiments, IC housing 49a includes a temperature-controlled zone or oven that accommodates separation column cartridge 42a'. A heating element may be provided to maintain the temperature surrounding the separation column independently of the ambient temperature surrounding the IC housing. The accurate and precise control of column temperature is generally important for achieving reproducible ion chromatographic separations of analyte ions of interests.

Figure 5B:
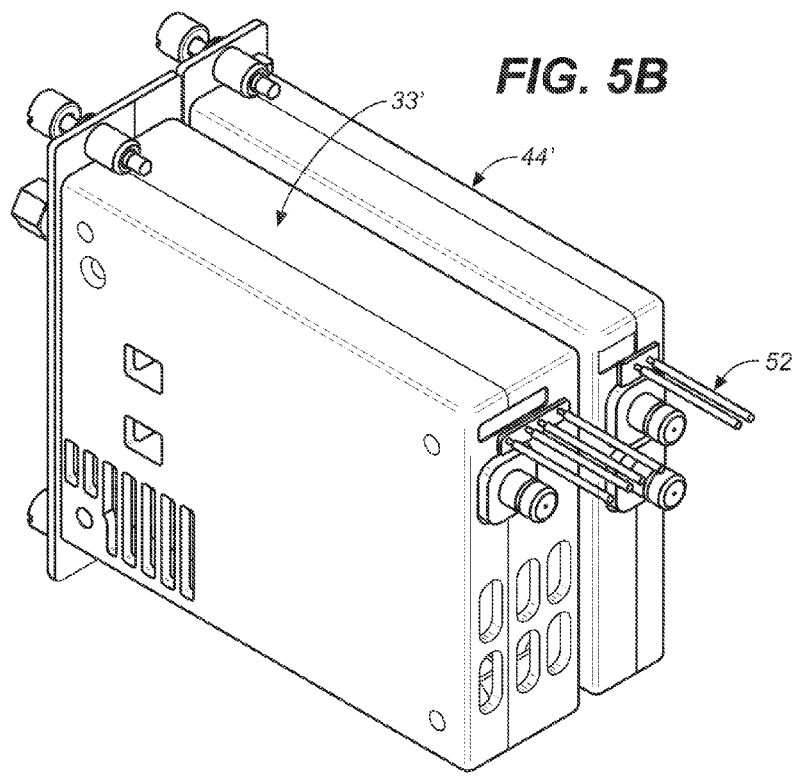
FIG. 5B is an enlarged view of the cartridges without the circuit boards, illustrating electrical pin connectors and fluid connectors.

Turning to FIG. 5, in various embodiments, a back panel of the IC housing 49a includes an array of pin connectors or receptacles 52 for establishing an electrical connection with cartridges 33' and 44'. In various embodiments, the pin connectors are Pogo™ pins. A Pogo™ pin is a device used in electronics to establish a connection between two printed circuit boards. The Pogo™ pin usually takes the form of a slender cylinder containing two sharp, spring-loaded pins. Pressed between two electronic circuits, the sharp points at each end of the pin make secure contacts with the two circuits at each end and thereby connect them together. Pogo™ is a registered trademark of Everett Charles Technologies (Pomona, Calif.).

In various embodiments, the rear end 60a of each component cartridge may be fitted with circuit board 58a in contact with one end of the pin connectors. An opposite end of the pins makes contact with a main circuit board on the IC housing back panel when the cartridge is engaged in the housing thereby establishing an electrical connection automatically. Instead of using conventional electrical cables and connectors requiring several manual steps to form the electrical connection, the pin connectors can be conveniently used to provide current and/or voltage power sources required for operation of various electrolytic system components such as an electrolytic eluent generator, an electrolytic suppressor, and the CR-TC through the IC housing assembly. Additionally, the pin type of electrical connections can be used in sensory circuits to detect the presence of system component cartridges. Thus, the main circuit board can control the system based on the presence or absence of a cartridge in the IC housing. The use of presence sensing functionality can also provide users with readiness and error indicators for their specific configurations.

With reference to FIGS. 2-5, IC housing 49a is a miniaturized chromatography compartment designed to house key chromatography components such as a high-pressure degasser assembly, a sample injector, a separation column, an electrolytic suppressor, a carbonate removal device (CRD). The volume of the IC housing may be in the range of about 1 cubic-inch to about 1000 cubic-inches. In various embodiments, the IC housing has physical dimensions of about 7.3 inch×about 3.7 inch×about 5.5 inch. The exemplary high-pressure degasser assembly cartridge 39' and CRD cartridge 44' each have physical dimensions of about 0.82 inch×about 3.68-inch×about 4.46 inch. The exemplary separation column cartridge 42' has dimensions of about 3.6 inch×about 1.5-inch×about 3.8 inch. The exemplary electrolytic suppressor cartridge 33' has dimensions of about 0.82 inch×about 3.68-inch×about 4.46 inch. By comparison, such components typically take up a volume in the range of 100 to 300 cubic-inches. In various embodiments, each dimension of the corresponding receiving slots in the housing for the respective cartridges is typically about 0.010 to about 0.040 inch larger than each dimension of the corresponding cartridges. Due to its small size, the IC housing offers unique advantages as a chromatography compartment in an ion chromatography system.

In one embodiment, the IC housing receives key system components, such as a high-pressure degasser assembly, a sample injector, a separation column, an electrolytic suppressor, a carbonate removal device (CRD), and a detector, and the IC housing is located remotely (i.e., 1 meter or more) from physically-larger components such as the pump and the system control computer of the ion chromatography system. With appropriate fluid and electrical communications between the IC housing and the pump and system control computer, the IC housing can be placed in a remote location that is not readily accessible or hazardous to system operators to perform ion chromatography separations. For example, the IC housing can be conveniently incorporated into a remote on-line analyzer for process monitoring in various industrial processes. The IC housing may be placed remotely in a radio-active environment to perform ion chromatography separation of target analytes with no risk of exposing the system operator to the hazardous conditions. Due to its small size and light weight, it is conceivable that the IC housing may be installed in a space vehicle to meet the need of determining the analytes of interest in space explorations.

Figure 6:
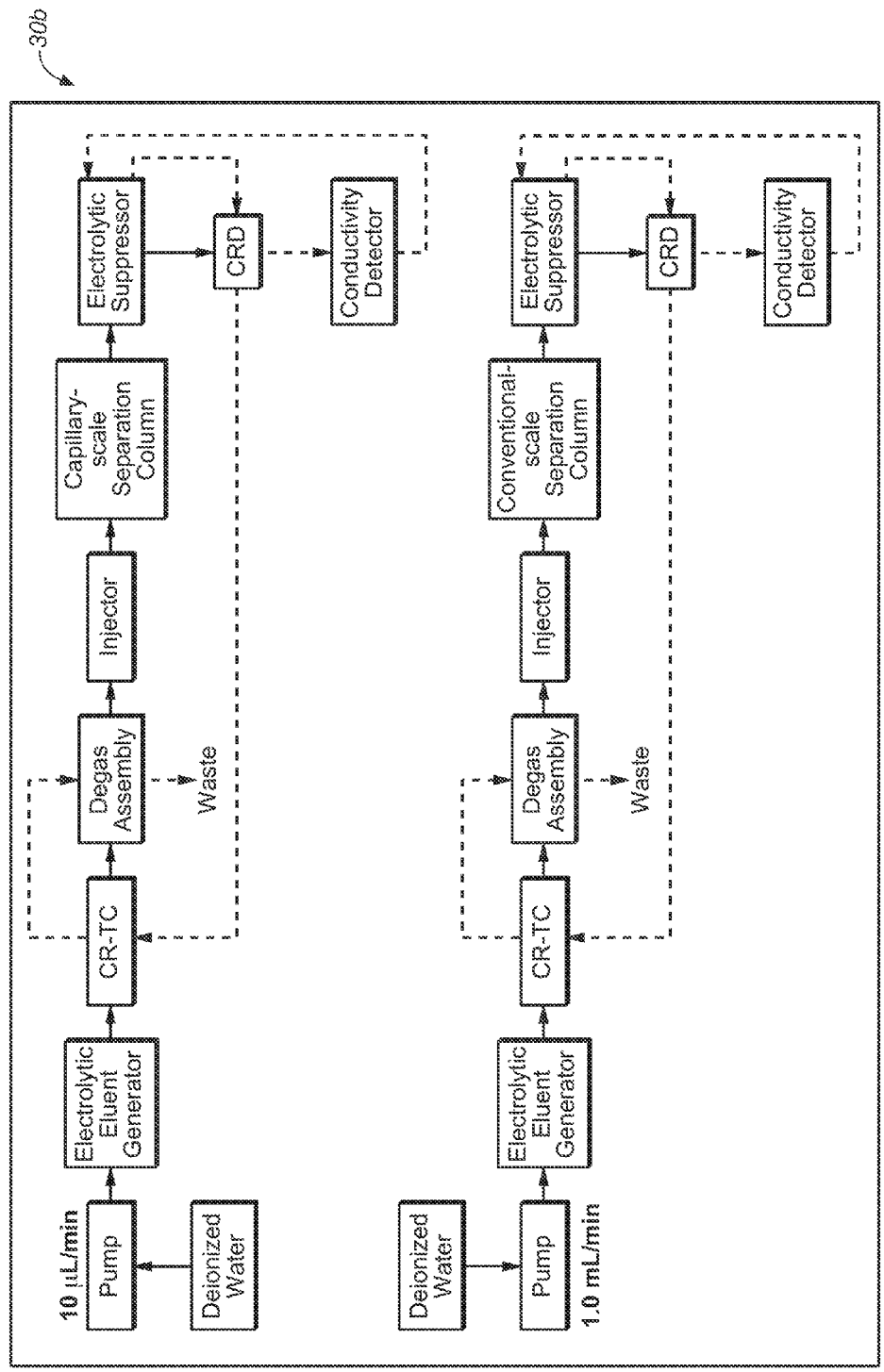
FIG. 6 is a block diagram of a dual-channel, multichannel ion chromatography system similar to that of FIG. 2, illustrating configuration of the system for performing both analytical-scale and capillary-scale ion chromatographic separations simultaneously in accordance with the present invention.

In various embodiments, capillary-scale ion chromatography system components—such as an electrolytic eluent generator, a CR-TC, a high-pressure degasser assembly, a sample injector, a separation column, an electrolytic suppressor, a carbonate removal device (CRD), and a detector—are used in conjunction with conventional-scale ion chromatography system components to construct a multichannel ion chromatography system. FIG. 6 illustrates a block diagram of a dual-channel, multichannel ion chromatography system 30b capable of performing both analytical-scale and capillary-scale ion chromatographic separations simultaneously. In this manner, the system in accordance with the present invention may be configured to provide resolution of species not possible with single-dimension systems. The system may also provide greater speed and efficiency.

Figure 7:
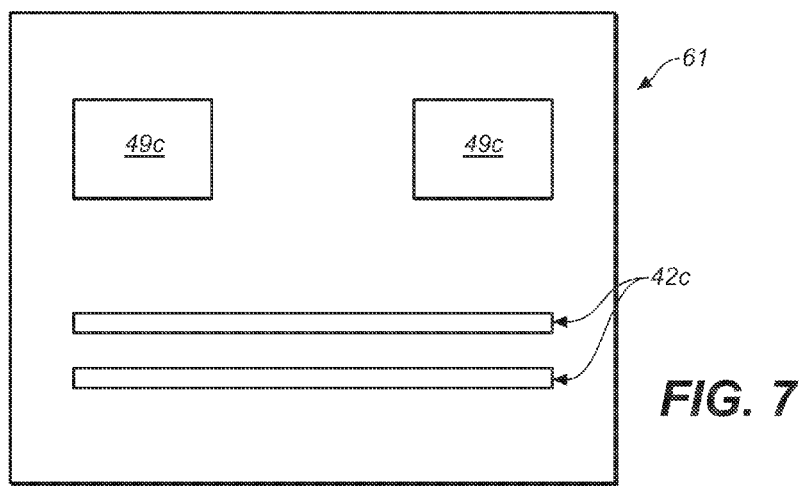
FIG. 7 is a block diagram of the system components of the multichannel ion chromatography system of FIG. 6, illustrating a conventional-scale compartment housing two exemplary IC cubes for two-dimensional ion chromatographic separations and two conventional-scale separation channels coupled to the capillary-scale separation channel in accordance with the present invention.

In various embodiments, the capillary-scale system components of the multichannel ion chromatography system are fitted into IC housing 49a as described above, and the IC housing is placed in a larger, conventional-scale chromatography compartment 61c that houses conventional-scale ion chromatography system components as illustrated in FIG. 7. Due to the smaller size of the IC housing, two or more IC housings may be placed inside the conventional-scale chromatography compartment. As shown in FIG. 7, the compartment may also house other components such as conventional-scale separation columns. In various embodiments, the exemplary system configured with two IC housings may be used to perform two capillary-scale IC separations simultaneously (e.g., two separation channels for anionic analytes, or two separation channels for cationic analytes, or one separation channels for anionic analytes and one separation channel for cationic analytes). In various embodiments, the conventional-scale ion chromatography separation channel can be conveniently coupled to the capillary-scale ion chromatography separation of another component, such as the IC housing, so that the multichannel ion chromatography system can perform two-dimensional ion chromatographic separations. One will appreciate that the IC housings may include one or more separation columns in the capillary-scale or conventional-scale. The IC compartment and/or housing may also be connected to other components of the IC system using tubes and other connections as would be understood by one of skill in the art from the description herein.

Figure 8:
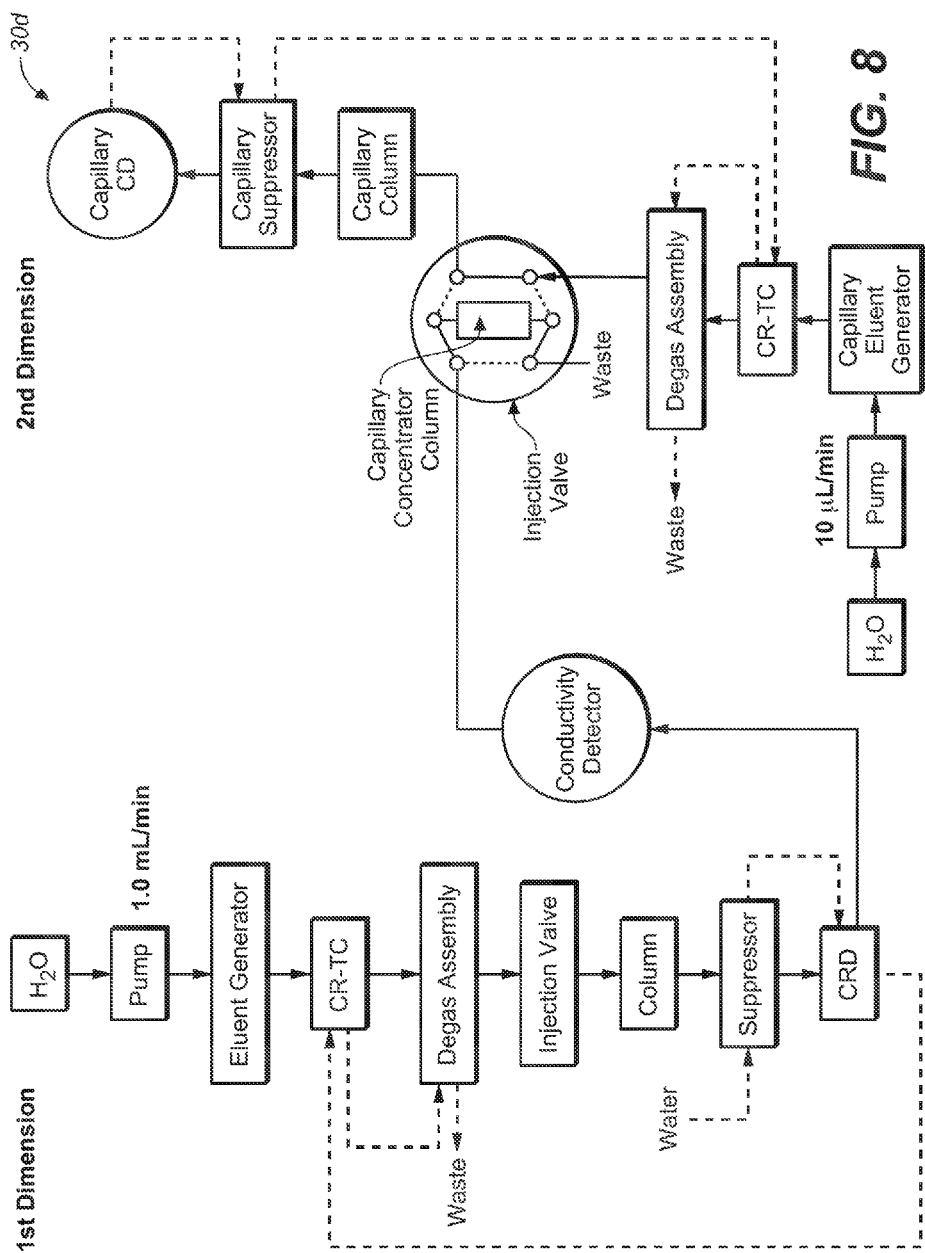
FIG. 8 is a block diagram of a multichannel ion chromatography system configured to perform two-dimensional ion chromatographic separations in accordance with the present invention, illustrating a conventional separation column in a first dimension and a capillary separation column in a second dimension.

FIG. 8 illustrates another multichannel ion chromatography system 30d that is configured to perform two-dimensional ion chromatographic separations. In this system, analyte ions are partially resolved from matrix ions on a conventional-scale IC column in the first dimension, collected onto a capillary concentrator column, then resolved from residual matrix ions on a capillary-scale IC column in the second dimension. In various embodiments, the conventional-scale IC column has about a 4 mm inner diameter (ID) and the capillary-scale IC column has about a 0.4 mm ID. It may be important to determine the optimum cut time from the first dimension to ensure that the target analyte is efficiently retained on the concentrator column before determining it in the second dimension. In various embodiments, the degasser assembly, separation column, and suppressor in the first dimension are all separately housed in cartridges engaged in an IC housing 49d similar to housing 49a described above. In various embodiments, the degasser assembly, separation column, and suppressor in the second dimension are all separately housed in cartridges engaged in an IC housing side-by-side with the first dimension IC housing.

In the exemplary system of FIG. 8, a predefined volume of suppressed effluent from the first separation dimension is concentrated on the capillary concentrator. Because the exemplary suppressed effluent from the hydroxide eluent in the first dimension is water, it provides an ideal environment for ion-exchange retention and concentration before the target analyte is transferred to the second dimension. The exemplary second-dimension column has only 1/100 the cross-sectional area of the first-dimension column, thus the detection sensitivity is theoretically enhanced by a factor of 100. One will appreciate that this type of multichannel ion chromatography system can be used to provide improved determination of analytes at trace concentrations (e.g., parts-per-trillion levels or ng/L levels) in complex sample matrices.

Figure 9:
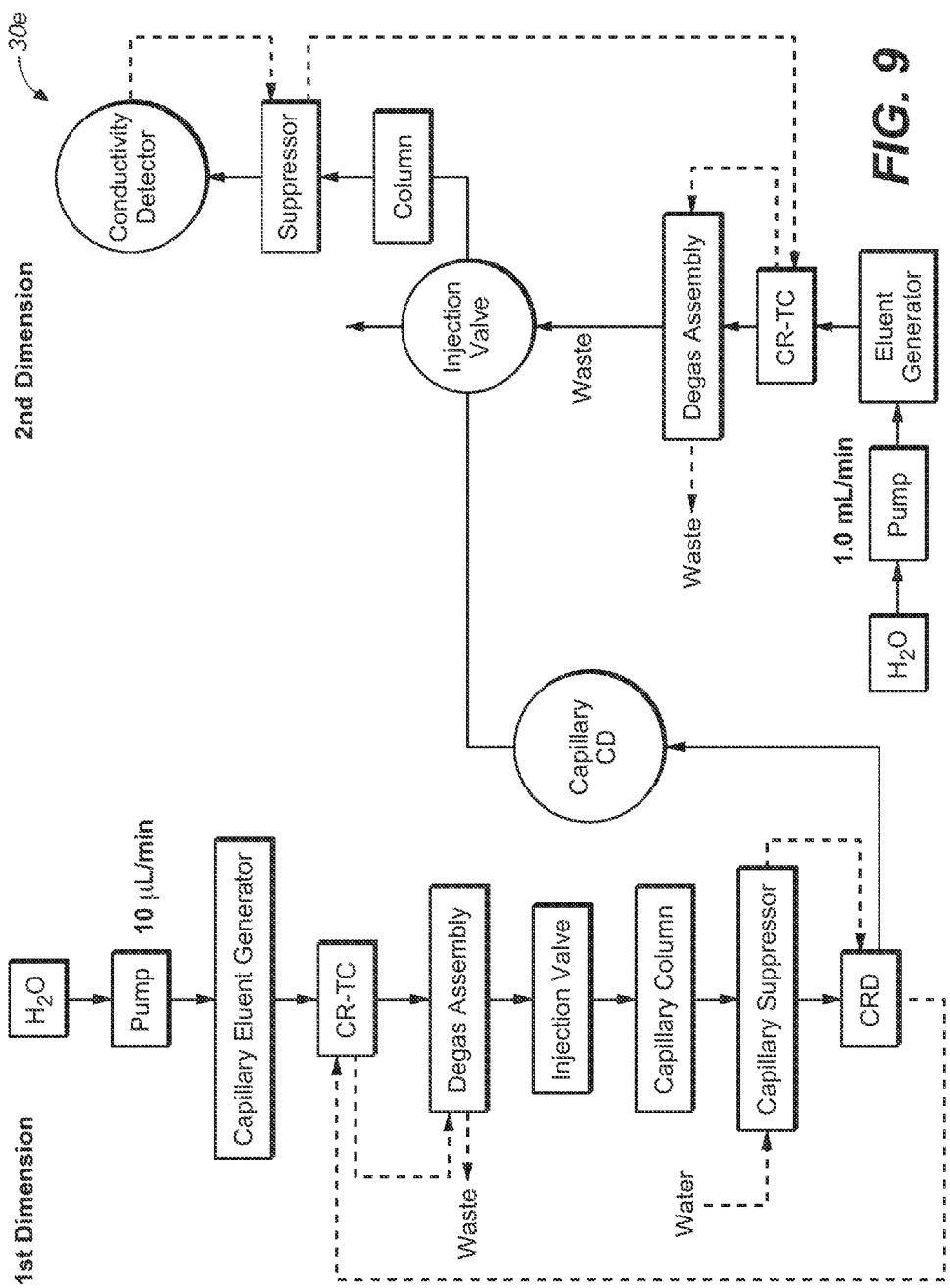
FIG. 9 is a block diagram of another multichannel ion chromatography system that is configured to perform two-dimensional ion chromatographic separations in accordance with the present invention, illustrating a capillary separation column in a first dimension and a conventional separation column in a second dimension.

FIG. 9 illustrates another multichannel ion chromatography system 30e that is configured to perform two-dimensional ion chromatographic separations. In this system, the sample of interest is injected into the first dimension separation channel and the separation of target analytes is performed using a capillary-scale IC column. In various embodiments, the capillary-scale IC column has about a 0.4 mm ID. The effluent from the first-dimension separation channel can be routed through the injection loop of the second-dimension separation channel that employs an analytical-scale IC column containing different stationary phase. In various embodiments, the analytical-scale IC column has about 2 mm to about 4 mm ID. In various embodiments, the degasser assembly, separation column, and suppressor in the first dimension are all separately housed in cartridges engaged in an IC housing similar to housing 49a described above. In various embodiments, the degasser assembly, separation column, and suppressor in the second dimension are all separately housed in cartridges engaged in an IC housing side-by-side with the first dimension IC housing.

In the exemplary system of FIG. 9, the second-dimension separation channel is used to provide the additional resolution of target analytes that can not be achieved in the first-dimension separation channel. It may be important to determine the optimum cut time from the first dimension to ensure that the fraction of the effluent in the sample loop of the second-dimension separation column contains the analytes of interest. This type of multichannel ion chromatography system can be used to provide improved determination—finer and/or broader range of resolution—of target analytes in complex sample matrices. Typically, complex samples would require performing two or more experiments on different, bulky systems.

The present invention provides a high level of modularity and flexibility. The components and configurations described above allow for easy substitution and changes to the system without complicated, cumbersome changes to the flow channel and other aspects of the system. One will appreciate from the description herein that the above-described system configurations may be achieved by the simple change of cartridges in the respective IC housing and/or the change of the IC housings in the IC compartment. The system of the present invention also allows for the use of modular capillary-scale components with conventional-scale components without the need for additional complicated devices to provide interoperability.

The method of using the ion chromatography system in accordance with the present invention is similar in many respects to conventional ion chromatography systems. As noted above, IC housing 49a may be connected to a conventional chromatography system and components and operated conventionally. Thus, the IC housing and system in accordance with the present provides a high level of interoperability with existing ion chromatography components.

The novel design of IC housing 49a with the regenerant manifold plate and the related component cartridges allows fast, simple insertion of key IC system components into the IC cube and provides automatic fluidic connections for regenerant flows. This significantly simplifies and reduces the number of manually-made fluid connections in an ion chromatography system. In the case of a capillary ion chromatography, this would be especially beneficial and improve the system's ease-of-use and reliability since making proper fluid connections can be particularly difficult to accomplish.

In operation and use, the system in accordance with the present invention is used for performing ion chromatography by generating an eluent from an electrolytic eluent generator, injecting an aqueous sample stream into the eluent, flowing the sample stream through a first separation column to chromatographically separate ionic species, and detecting the resolved ionic species from the first separation column. Various aspects of the system of the present invention and its operation are similar to that disclosed by U.S. patent application Ser. No. 11/229,002 filed Sep. 16, 2005 and entitled Multidimensional Chromatography Apparatus and Method, which published as U.S. Pub. No. 2007/0065343, the entire content of which is incorporated herein for all purposes by reference. In various embodiments, the system is configured for performing ion chromatography in two dimensions by further concentrating the sample stream in a concentrator column and performing a separation in a second dimension. In various embodiments, the system includes two or more IC housings such that separations in two dimensions are performed simultaneously.

These features and other features of the present invention improve the ease-of-use and reliability of the ion chromatography system. The capillary ion chromatography systems in accordance with the present invention provide miniaturized chromatography compartments and simplified fluid connections.

The multichannel ion chromatography systems described above provide improved means for fluid connections to make capillary ion chromatography a more easy-to-use and reliable analytical technique. The various embodiments of multichannel ion chromatography systems offer the flexibility to perform two or more independent separation processes in either capillary-scale or conventional-scale simultaneously. In addition, the systems in accordance with the present invention offers improved and easy-to-use integration of ion chromatographic separation processes at conventional flow rates and capillary flow rates for two-dimensional ion chromatographic separations. These systems are suitable for determination of target ionic analytes in a variety of complex sample matrices.

The system and method of the present invention allow for the practice of ion chromatography in the capillary format (i.e., using columns with internal diameters of 1 mm or smaller). In part, the system provides a modular format and consumables for working in the capillary format with existing IC components. One will appreciate that the capillary format can bring out a number of advantages for analysis of ionic analytes. The use of a capillary separation column improves the separation efficiency and/or speed. Separation processes in the capillary format require a significantly smaller amount of sample and thus offer improved compatibility with applications where the amount of sample is limited and an injection of, for example, 10 µL sample can become a large-loop injection in capillary IC. Capillary ion chromatography systems in accordance with the present invention typically operate at about 1 µL/min to about 100 µL/min and thus the amount of eluent consumed is very small. The capillary ion chromatography system has improved capability for continuous operation with minimal intervention and thus minimizes problems associated with system start-up and shutdown. The operation of capillary ion chromatography at low flow rates improves the system compatibility with mass spectrometers. Capillary ion chromatography in accordance with the present invention is also expected to offer ease of use, higher sample throughput, and improved calibration. In addition, the practice of ion chromatography in the capillary format opens the door for the possibilities of offering new selectivity for difficult applications using new columns packed with more costly and difficult-to-make stationary phases.

EXAMPLES

The invention is further illustrated by the Examples that follow. The Examples are not intended to define or limit the scope of the invention.

Example 1

Use of a Multichannel Ion Chromatography System Containing an IC Cube for Separation of Common Anions on a Capillary Anion Exchange Separation Column In this example, a multichannel ion chromatography system was constructed using ICS-3000 ion chromatography system component modules from Dionex Corporation, Sunnyvale, Calif. including a pump module, electrolytic eluent generator (EG) module, and a conventional-scale chromatography compartment (DC) module. A Dionex Chromeleon 6.8 chromatography data system was used for instrument control, data collection, and processing. An IC housing based on the embodiment illustrated in FIG. 2 was also constructed. The IC housing has a physical dimension of about 7.3 inch× about 3.7 inch×about 5.5 inch. The IC housing was prepared to include capillary-scale system components such as a high-pressure degasser assembly, a sample injector, a separation column, an electrolytic suppressor, and a carbonate removal device (CRD). The IC housing was physically placed in the upper compartment of the ICS-300 DC module. The DC was modified to provide electronic control necessary to operate the injection valve, the electrolytic suppressor, and the column heater of the IC cube. The detection of analytes was accomplished using an ICS-3000 conductivity detector that was modified to include a capillary conductivity cell to be compatible with capillary-scale separations. In this system, a capillary-scale electrolytic eluent generator and a capillary CR-ATC was installed in the modified ICS-3000 EG module and controlled by the modified ICS-3000 EG module.

Figure 10:
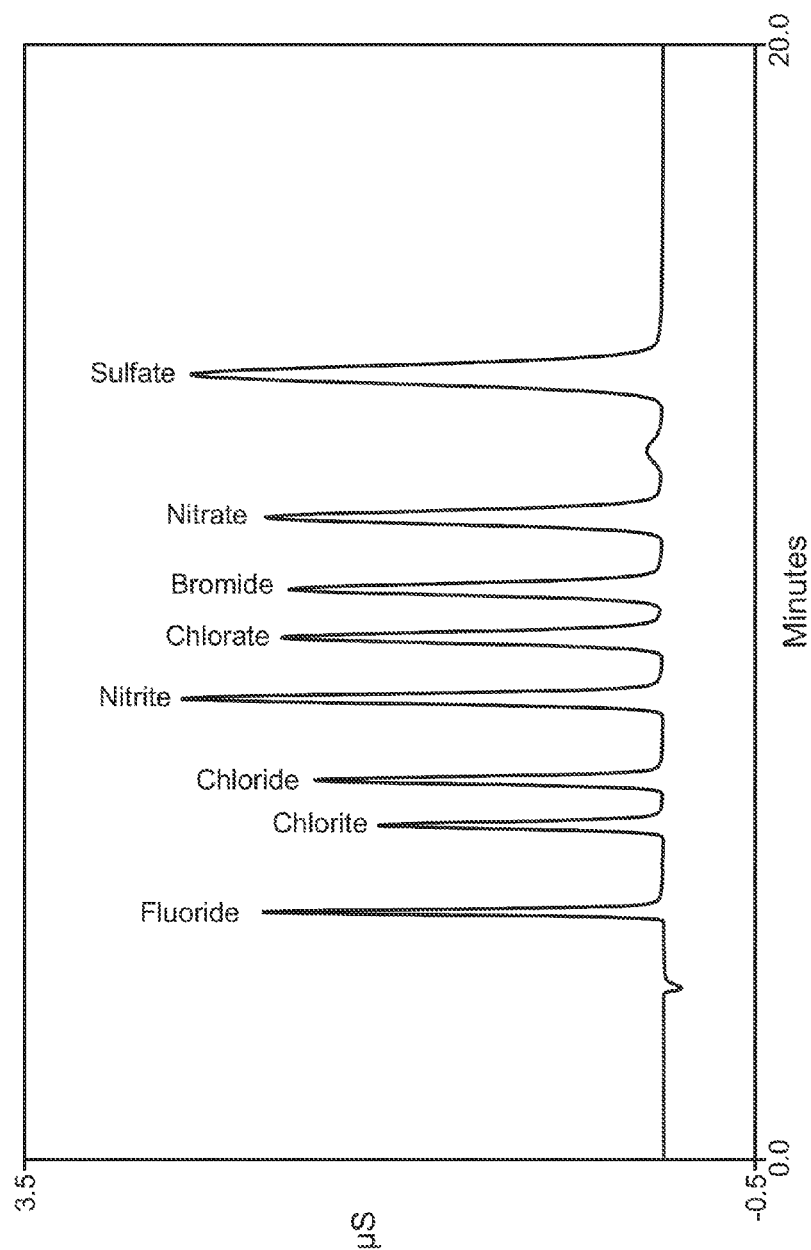
FIG. 10 is a graphical representation of the results of the separation of 8 common anions obtained using a multichannel ion chromatography system fitted with a capillary IC cube in accordance with the present invention.

In this example, the IC housing was also fitted with a capillary-scale separation column (0.4 mm×250 mm) packed with the Dionex AS19 anion exchange resin. FIG. 10 shows the separation of 8 common anions including fluoride, chlorite, chloride, nitrite, chlorate, bromide, nitrate, and sulfate obtained using the system under the eluting condition of 20 mM KOH at 10 µL/min. FIG. 10 shows an overlay of 30 consecutive separations of the target analytes. The results show highly reproducible separation of the target anions with analyte retention percent relative standard deviation (RDS) ranging from 0.047% for nitrite to 0.078% for sulfate, and analyte peak area percent RSD ranging from 0.28% for fluoride to 0.33% for bromate. These results demonstrate the multichannel ion chromatography system described in this invention can be used to provide reliable capillary-scale ion chromatographic separation of target anionic analytes using only deionized water as the carrier streams.

Example 2

Figure 11:
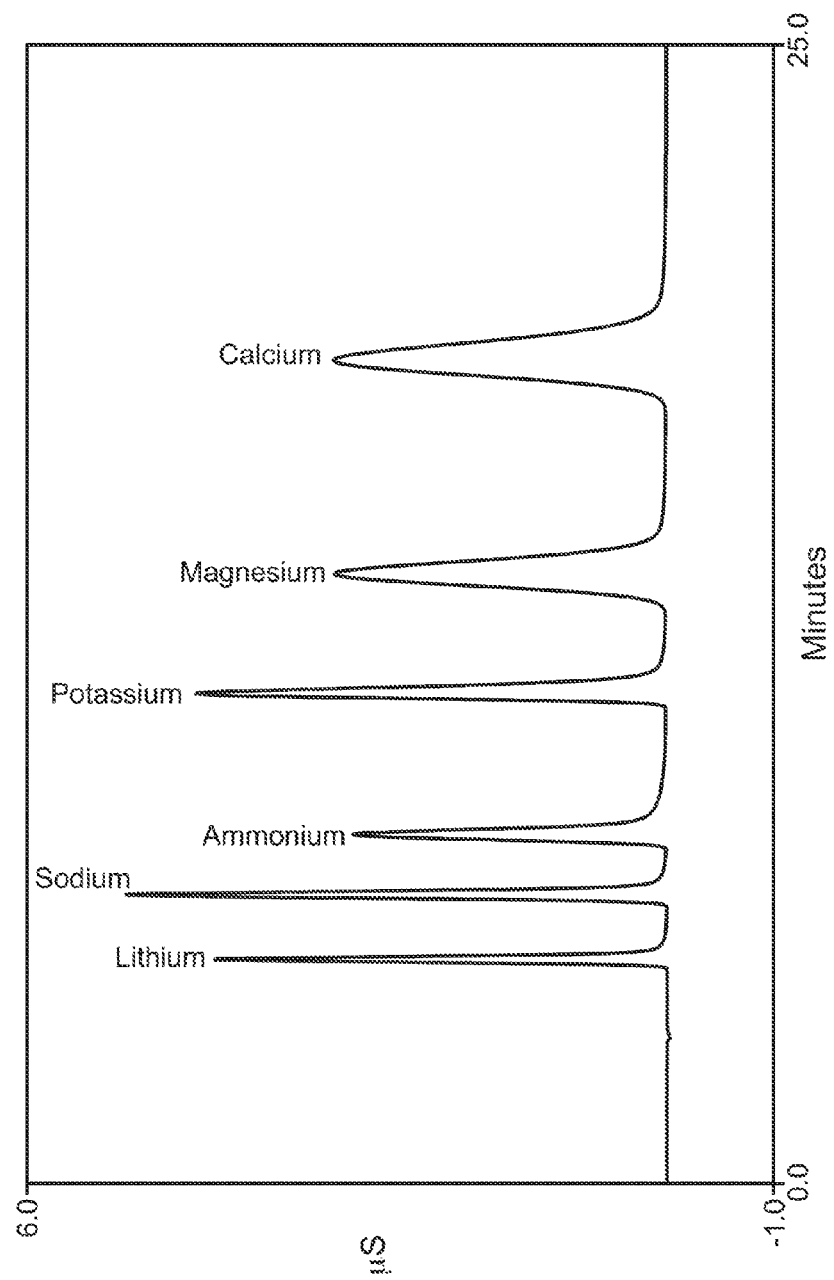
FIG. 11 is a graphical representation of the results of the separation of 6 common cations obtained using the system of FIG. 10.

Use of a Multichannel Ion Chromatography System Containing an IC Cube for Separation of Common Cation on a Capillary Cation Exchange Separation Column In this example, the multichannel ion chromatography system described in Example 1 was used. The IC cube was fitted with a capillary separation column (0.4 mm×250 mm) packed with the Dionex CS16 cation exchange resin. FIG. 10 shows the separation of 6 common cations including lithium, sodium, ammonium, potassium, magnesium, and calcium obtained using the system under the eluting condition of 30 mM methanesulfonic acid at 10 µL/min. FIG. 11 shows an overlay of 30 consecutive separations of the target analytes. The results show highly reproducible separation of the target cations with analyte retention percent relative standard deviation (RDS) ranging from 0.052% for magnesium to 0.072% for sodium, and analyte peak area percent RSD ranging from 0.33% for sodium to 0.46% for calcium. These results demonstrate the multichannel ion chromatography system described in this invention can be used to provide reliable capillary-scale ion chromatographic separation of target cationic analytes using only deionized water as the carrier streams.

Example 3

Figure 12:
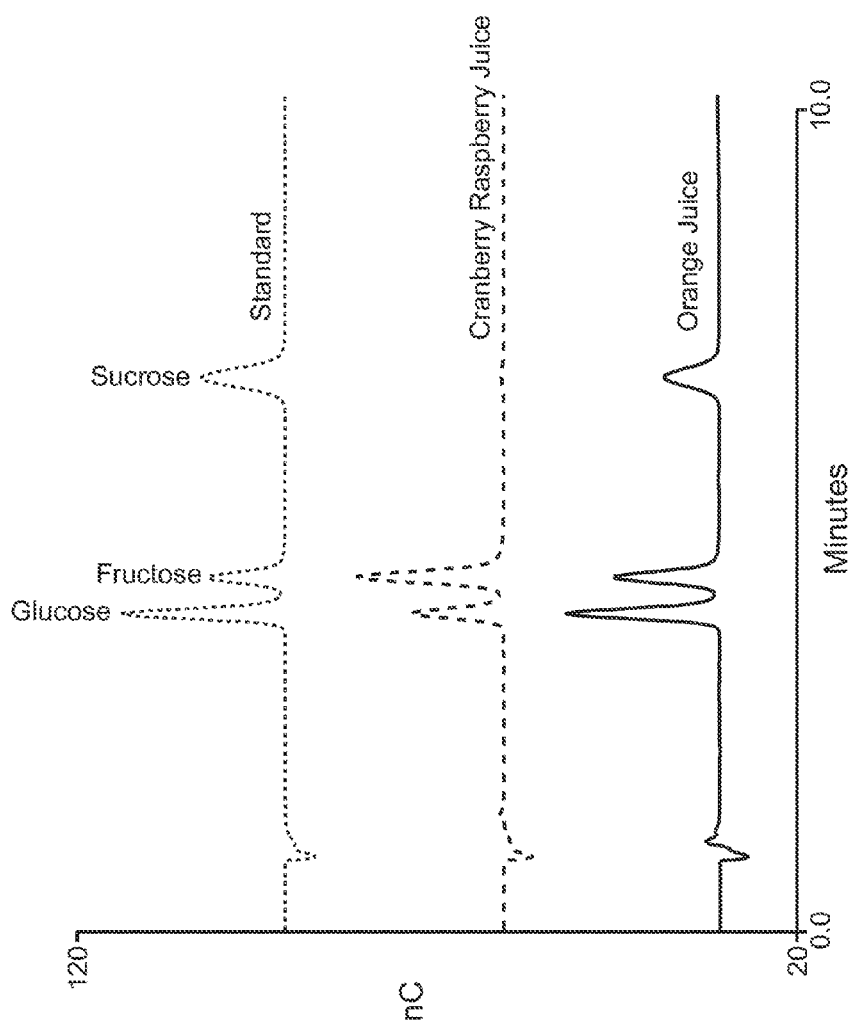
FIG. 12 is a graphical representation of the results of the separation of monosaccharides and disaccharides from juice samples obtained using a multichannel ion chromatography system fitted with a capillary IC cube in accordance with the present invention.

Use of a Multichannel Ion Chromatography System Containing an IC Cube for Determination of Sugars in Juice Samples a Capillary Anion Exchange Separation Column In this example, a multichannel ion chromatography system similar to the one described in Example 1 was used. The detection of analytes was accomplished using an ICS-3000 electrochemical detector that was modified to include a capillary flow cell to be compatible with capillary-scale separations. The electrochemical detector was operated in the pulse amperometric detection mode. The IC housing was fitted with a capillary-scale separation column (0.4 mm×150 mm) packed with the Dionex CarboPac PA20 anion exchange resin. FIG. 12 shows the separation of glucose, fructose, and sucrose in juice samples obtained using the system under the eluting condition of 50 mM KOH at 10 μL/min.

Example 4

Figure 13:
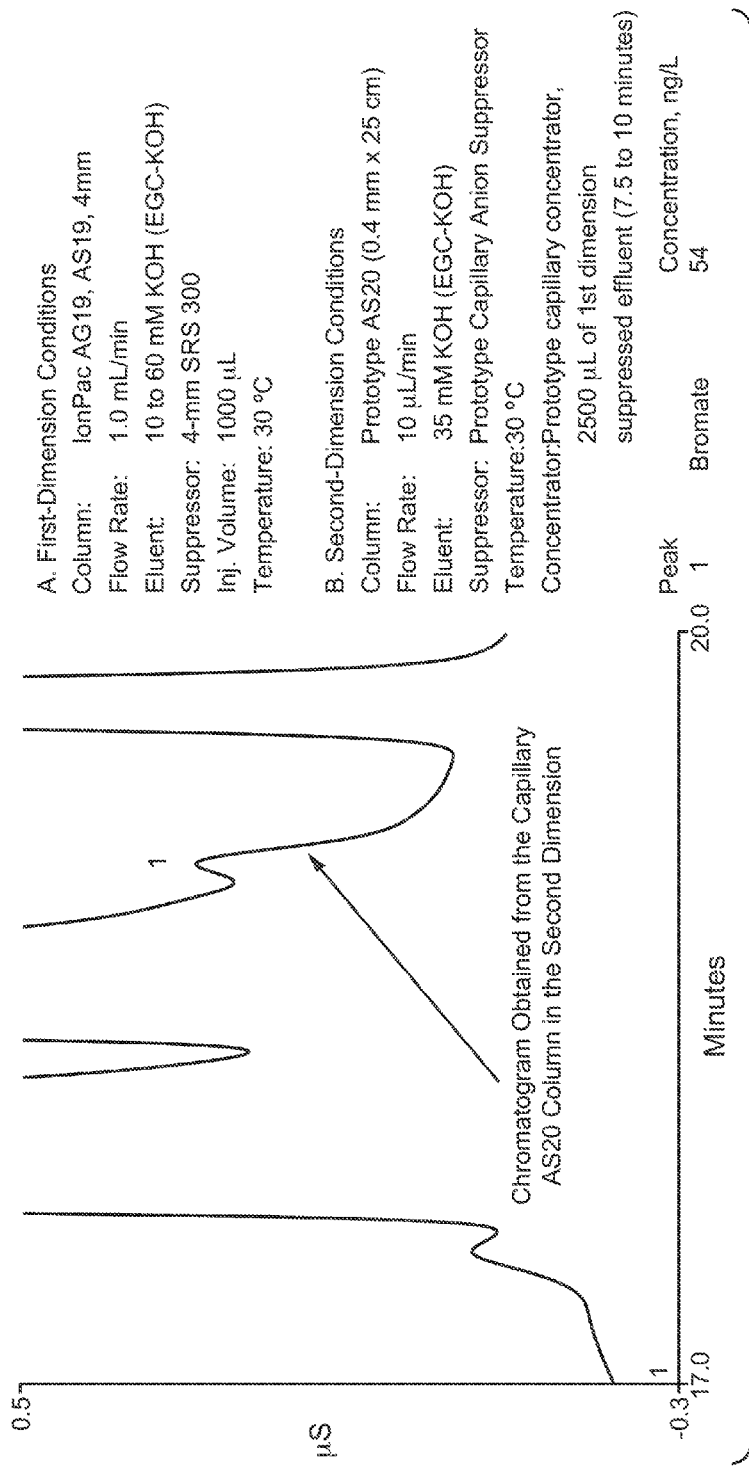
FIG. 13 is a graphical representation of the results of the separation of trace bromate from a bottled water sample obtained using two-dimensional IC separations on the system of FIG. 10.

Determination of Trace Bromate in a Bottled Water Sample Using a Multichannel Ion Chromatography System In this example, the multichannel ion chromatography system described in Example 1 was used. The IC housing was fitted with a capillary-scale separation column (0.4 mm×250 mm) packed with the Dionex AS20 anion exchange resin. A conventional-scale Dionex AS19 column (4-mm×250 mm) was also used. This system was used to determine trace level of bromate in drinking water samples. In this example, 1000 μL of sample was injected into the 4-mm IonPac AG19/AS19 columns in the first separation dimension. Bromate ions are partially resolved from matrix ions, collected onto a capillary concentrator column, then resolved from residual matrix ions on a capillary 0.4-mm AS20 column) in the second dimension. In this example, it is important to determine the optimum cut time from the first dimension to ensure that the target analyte is efficiently retained on the concentrator column before determining it in the second dimension. In this example, the cut time window of 7.5 min to 10 min was used to load 2500 μL of the first-dimension effluent onto the capillary concentrator column. FIG. 13 shows the chromatogram obtained from the capillary AS20 column when the multichannel IC system was used to determine trace-level bromate in a bottled water sample. The concentration of bromate was found to be 54 ng/L in the bottle water sample. The above results demonstrate that the multichannel ion chromatography system described in this invention can be configured as a two-dimensional ion chromatography system to determine target analytes at trace levels.

For convenience in explanation and accurate definition in the appended claims, the terms "up" or "upper", "down" or "lower", "inside" and "outside" are used to describe features of the present invention with reference to the positions of such features as displayed in the figures.

In many respects the modifications of the various figures resemble those of preceding modifications and the same reference numerals followed by subscripts "a", "b", "c", and "d" designate corresponding parts.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. An apparatus for ion chromatography (IC) comprising:
a sample injector for providing a sample having a target analyte or target analytes;
an IC separation column for separating ionic species in the sample, the separation column housed within a separation column cartridge, wherein the sample injector is positioned adjacent to and in fluid communication with the separation column cartridge;
a suppressor for reducing a conductance of an eluent and enhancing the conductance of the target analyte, the suppressor housed within a suppressor cartridge;
a miniaturized IC housing including predefined respective separation column and suppressor slots formed within the miniaturized IC housing for removably receiving the corresponding separation column cartridge and suppressor cartridge and a manifold plate fixed on a back panel of the miniaturized IC housing and extending across both the separation column slot and the suppressor slot for fluidly connecting the separation column cartridge and suppressor cartridge received in the predefined slots; and
a plurality of quick connect/disconnect fluid connectors, each fluid connector fluidly interconnecting the manifold plate with a respective one of the separation column cartridge and the suppressor cartridge, wherein the separation column cartridge is automatically fluidly interconnected with the manifold plate when inserted into the separation column slot, and wherein the suppressor cartridge is automatically fluidly interconnected with the manifold plate when inserted into the suppressor slot.

2. The apparatus of claim 1, further comprising a high-pressure degasser assembly cartridge for removing gas from the eluent, wherein the high-pressure degasser assembly cartridge is removably received by the miniaturized IC housing in a predefined degasser slot formed within the miniaturized IC housing.

3. The apparatus of claim 2, further comprising a carbonate removal device cartridge fluidly connected to the suppressor, wherein the degasser assembly cartridge and carbonate removal device cartridge are received in carbonate removal device and degasser assembly slots formed within the miniaturized IC housing.

4. The apparatus of claim 1, further comprising a regenerant manifold plate attached to the quick fluid connectors of at least two of the cartridges and configured to direct a regenerant flow among the respective cartridges.

5. The apparatus of claim 1, further comprising a temperature-controlled zone in the housing for maintaining a temperature of the separation column cartridge.

6. The apparatus of claim 5, wherein the temperature-controlled zone includes a heating element.

7. The apparatus of claim 1, wherein each of the respective cartridges comprises a circuit board for controlling respective internal components.

8. The apparatus of claim 7, wherein each of the respective cartridges comprises at least one electrical pin connector connected at one end to the respective circuit board and including an opposite end to establish an electrical connection with a main circuit board provided in the housing when the respective cartridge is engaged within the housing.

9. The apparatus of claim 1, wherein the housing is block-shaped and has a volume in the range of about 1 cubic inch to about 1000 cubic inches.

10. The apparatus of claim 1, wherein the miniaturized IC housing is configured for insertion into an IC compartment of an ion chromatography system.

11. The apparatus of claim 10 in combination with a second IC apparatus housed within a second housing, wherein the first and the second housings are positioned side-by-side in the IC compartment of the ion chromatography system.

12. The apparatus of claim 11, wherein the second IC apparatus is configured for finer resolution than the first IC apparatus.

13. A system for ion chromatography comprising:
the apparatus of claim 3;
an eluent generator driven by a pump for delivering eluent to the sample injector; and
a detector fluidly connected to the suppressor, directly or via the carbonate removal device, for detecting a resolved ionic species.

14. The system of claim 13, wherein the apparatus, eluent generator, and detector are capillary-scale components and the pump is conventional-scale.

15. The system of claim 13, further comprising:
a concentrator column for receiving and concentrating treated effluent from the IC separation column;
a second IC separation column in fluid communication with the concentrator column;
a second suppressor in fluid communication with the second separation column; and
a second detector for detecting a resolved ionic species from the second suppressor.

16. The system of claim 13, wherein the concentrator column, second IC separation column, and second suppressor are housed in the housing.

17. A method of performing ion chromatography comprising:
loading the system of claim 13 with a sample;
flowing the sample in the system; and
detecting resolved species in the detector.

18. A system for ion chromatography comprising:
a sample injector for delivering a sample including a target analyte or target analytes;
an eluent generator for delivering eluent to the sample injector;
an IC housing assembly comprising:
a degasser assembly cartridge including a high-pressure degasser assembly for removing gas from the eluent;
an IC cartridge including an IC separation column for separating ionic species;
a suppressor cartridge including a suppressor for reducing the conductance of the eluent and enhancing the conductance of the target analyte; and
a miniaturized housing including predefined slots formed within the miniaturized IC housing for removably receiving each of the cartridges and a manifold plate fixed on a back panel of the miniaturized IC housing and extending across the predefined slots for fluidly connecting the cartridges received in the predefined slots;
a plurality of quick connect/disconnect fluid connectors, each fluid connector fluidly interconnecting the manifold plate with a respective one of the degasser assembly cartridge, the IC cartridge and the suppressor cartridge, wherein each respective cartridge is automatically fluidly interconnected with the manifold plate when inserted into a respective predefined slot; and
a detector fluidly connected to the suppressor for detecting a resolved ionic species.

19. The system of claim 18, wherein the IC housing further comprises a carbonate removal device cartridge fluidly connected to the suppressor and detector.

20. The system of claim 18, further comprising:
a second IC housing assembly connected to a second injector and second eluent generator, the second IC housing assembly comprising a second degasser assembly, a second IC separation column, a second suppressor, and a second carbonate removal device; and
a second detector fluidly connected to the suppressor for detecting a resolved ionic species,
wherein the first separation column is a capillary-scale separation column and the second separation column is a conventional-scale separation column.

* * * * *